US011020413B2

(12) United States Patent
Sangild

(10) Patent No.: US 11,020,413 B2
(45) Date of Patent: *Jun. 1, 2021

(54) COMPOSITIONS FOR USE IN THE PREVENTION OR TREATMENT OF NECROTIZING ENTEROCOLITIS IN INFANTS AND YOUNG CHILDREN

(71) Applicant: NESTEC S.A., Vevey (CH)

(72) Inventor: Per Torp Sangild, Copenhagen NV (DK)

(73) Assignee: Societe des Produits Nestle S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/036,854

(22) PCT Filed: Nov. 14, 2014

(86) PCT No.: PCT/EP2014/074584
§ 371 (c)(1),
(2) Date: May 16, 2016

(87) PCT Pub. No.: WO2015/071403
PCT Pub. Date: May 21, 2015

(65) Prior Publication Data
US 2016/0296541 A1    Oct. 13, 2016

(30) Foreign Application Priority Data

Nov. 15, 2013 (EP) ..................................... 13193056

(51) Int. Cl.
A61K 31/702     (2006.01)
A23L 33/00      (2016.01)
A23L 33/135     (2016.01)
A61K 35/747     (2015.01)
A61K 35/745     (2015.01)
A23L 33/10      (2016.01)
A23L 33/125     (2016.01)
A61K 35/741     (2015.01)

(52) U.S. Cl.
CPC ............ *A61K 31/702* (2013.01); *A23L 33/10* (2016.08); *A23L 33/125* (2016.08); *A23L 33/135* (2016.08); *A23L 33/40* (2016.08); *A61K 35/741* (2013.01); *A61K 35/745* (2013.01); *A61K 35/747* (2013.01); *A23V 2002/00* (2013.01); *A23Y 2220/43* (2013.01); *A23Y 2220/63* (2013.01); *A23Y 2220/73* (2013.01); *A23Y 2240/65* (2013.01); *A23Y 2300/29* (2013.01); *A23Y 2300/45* (2013.01); *A23Y 2300/49* (2013.01); *A23Y 2300/55* (2013.01)

(58) Field of Classification Search
None
See application file for complete search history.

(56) References Cited

U.S. PATENT DOCUMENTS

2012/0172319 A1   7/2012  Chow et al.
2012/0207882 A1   8/2012  Sonnenburg

FOREIGN PATENT DOCUMENTS

EP      1974743       10/2008
EP      2454948       5/2012
WO      2013057062    4/2013

OTHER PUBLICATIONS

Thurl et al., British Journal of Nutrition (2010), vol. 104, pp. 1261-1271.*
Asakuma et al., European Journal of Clinical Nutrition (2008) 62, pp. 488-494.*
DeLeoz et al., Journal of proteome research, 2012, vol. 11, pp. 4662-4672 (Year: 2012).*
Zhang et al., "Guidance for Nurturing Infants and Children", China Women Publishing House, 1st Edition, 2006, p. 45.
China Office Action Received for Application No. 201480062158. X, dated Feb. 21, 2020, 10 pages(5 pages of English translation and 5 pages of official copy).

* cited by examiner

Primary Examiner — Scott Long
Assistant Examiner — Evelyn Y Pyla
(74) Attorney, Agent, or Firm — K&L Gates LLP

(57) ABSTRACT

The invention discloses a composition comprising LNT and at least another human milk oligosaccharide or precursor thereof, for use in preventing and/or treating necrotizing enterocolitis in infants and young children.

13 Claims, 1 Drawing Sheet

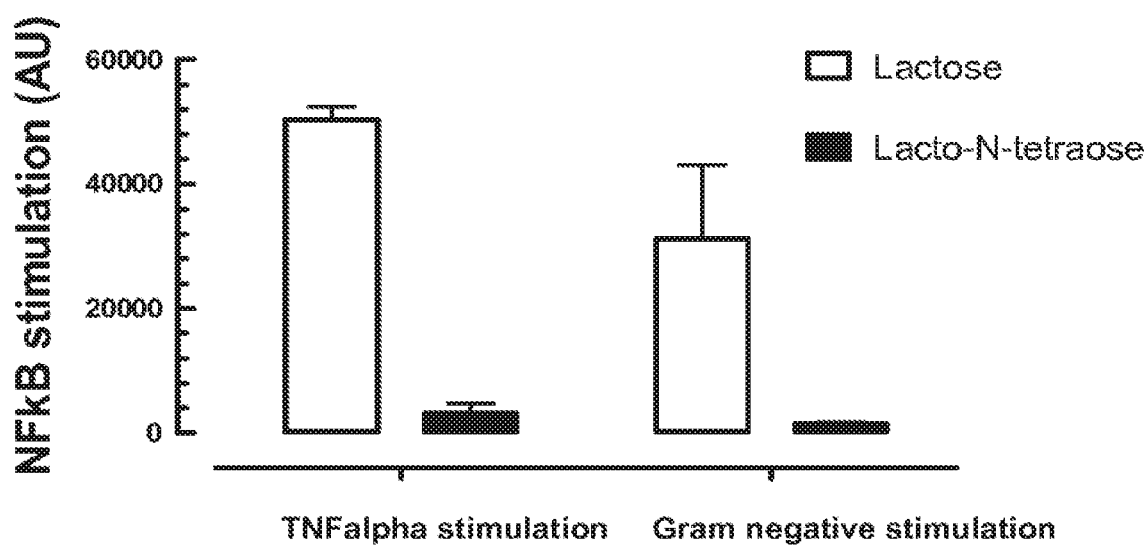

COMPOSITIONS FOR USE IN THE PREVENTION OR TREATMENT OF NECROTIZING ENTEROCOLITIS IN INFANTS AND YOUNG CHILDREN

CROSS REFERENCE TO RELATED APPLICATIONS

The present application is a National Stage of International Application No. PCT/EP2014/074584, filed on Nov. 14, 2014, which claims priority to European Patent Application No. 13193056.2, filed Nov. 15, 2013, the entire contents of which are being incorporated herein by reference.

FIELD OF THE INVENTION

This invention relates to compositions to prevent necrotizing enterocolitis in infants and young children and/or to decrease the duration, the risks, the complications and/or the severity of necrotizing enterocolitis in infants and young children, and/or to relieve the symptoms caused by necrotizing enterocolitis on health in infants and young children. This invention also relates to compositions that can be used for example to promote enteral feeding tolerance and gut functional maturation.

BACKGROUND OF THE INVENTION

Immaturity of the newborn's gastrointestinal tract functions is a risk factor for inflammatory diseases such as necrotizing enterocolitis or NEC, which is a serious disease of the gastrointestinal tract in neonates. It is associated with several complications like intestinal necrosis that could lead to resection of a part of the intestine, growth and developmental delay, problems of neurodevelopment, such as a long term neurodevelopment impairment, but also with high mortality (up to 20%) and morbidity.

The incidence of the condition is increased with prematurity and low birth weight infants. One reason is the combination of gut functional immaturity and the bacterial colonization of their gut that can easily destabilize the system manifest as enteral feeding intolerance seen as regurgitation and diarrhea and also in severe cases as NEC. Among the igniting factors are the overgrowths of microorganisms such as Enterobacteriacae and coagulase-negative staphylococci. NEC is a complex condition but the action of intestinal flora and gut immaturity are widely established and accepted as pathogenic factors.

Many attempts have been made to prevent NEC in infants. Through prevention of bacterial migration across the mucosa, competitive exclusion of pathogenic bacteria and enhancement of the immune responses of the host, the use of probiotics has been investigated. Gitish Deshpande et al in *Probiotics for prevention of necrotizing enterocolitis in preterm neonates with very low birthweight: a systematic review of randomised controlled trials*, Lancet 2007; 369 (9573) 1614-20, describes that probiotics might reduce the risk of necrotising enterocolitis in preterm neonates with less than 33 weeks' gestation. But it also states that the short-term and long-term safety of probiotics needs to be assessed in large trials and there are unanswered questions such as the dose, duration, and type of probiotic agents used for supplementation. However some other studies on probiotics have not been conclusive, for example Carlo Dani et al, in *Probiotics feedings in prevention of urinary tract infection, bacterial sepsis and necrotizing enterocolitis in preterms infants*, Biol Neonate 2002, 82:103-108, come to the conclusions that seven days of *lactobacillus* GG supplementation starting with the first feed is not effective in reducing the incidence of NEC in preterms infants.

Other pathways have therefore been explored such as the use of oligosaccharides, and especially human milk oligosaccharides. Human milk oligosaccharides (HMOs) are, collectively, the third largest solid constituents in human milk, after lactose and fat. HMOs usually consist of lactose at the reducing end with a carbohydrate core that often contains a fucose or a sialic acid at the non-reducing end. There are approximately one hundred different milk oligosaccharide structures that have been characterized in human milk.

Mother's milk is recommended for all infants. However, in some cases breast feeding is inadequate or unsuccessful for medical reasons or the mother chooses not to breast feed. Infant formulae have been developed for these situations.

Several infant formulae have been developed using HMO ingredients, such as fucosylated oligosaccharides, lacto-N-tetraose, lacto-N-neotetraose, or sialylated oligosaccharides, and for different purposes.

WO2009/077352 relates to a composition suitable in the prevention of opportunistic infections comprising a probiotic *Bifidobacterium* in association with a fucosylated oligosaccharide such as 2'FL. Respiratory, urinary and gastrointestinal tracts infections such as NEC are cited amongst the opportunistic infections that may be prevented.

WO2012/092156 discloses methods for decreasing the incidence of NEC in infants, toddlers or children using human milk oligosaccharides. A very large list of HMOs and precursors thereof is listed in this application, as well as many various combinations of HMOs and precursors thereof, and also many combinations of HMOs with one or several prebiotic oligosaccharides (FOS, GOS, inulin, polydextrose and/or gum). Some probiotics can also be added in the formulations. The possibility of combinations is however very wide in WO2012/092156, which also gives very little guidance regarding the amounts of the HMOs or precursors thereof that should be used to get an efficient result.

There is therefore a need to develop specific nutritional compositions suitable to prevent necrotizing enterocolitis in infants and young children and/or to treat necrotizing enterocolitis in infants and young children and/or suitable to promote enteral feeding tolerance and gastrointestinal functional maturation in infants and young children.

There is also a need to deliver such health benefits in a manner that is particularly suitable for these young subjects (infants and young children), in a manner that does not involve a classical pharmaceutical intervention as infants and young children are particularly fragile.

There is a need to deliver such health benefits in these young subjects in a manner that does not induce side effects and/or in a manner that is easy of deliver, and well accepted by the parents or health care practitioners.

There is also a need to deliver such benefits in a manner that does keep the cost of such delivery reasonable and affordable by most.

SUMMARY OF THE INVENTION

The present inventors have surprisingly found that a composition comprising a mixture of specific human milk oligosaccharides is particularly effective for use (i) in promoting enteral feeding tolerance and gastrointestinal functional maturation and (ii) in decreasing the incidence of necrotizing enterocolitis in infants and young children.

Accordingly, the present invention provides a composition comprising LNT with at least another HMO or precursor thereof, for use in preventing necrotizing enterocolitis in infants and young children and/or in treating necrotizing enterocolitis in infants and young children (such as decreasing the duration, the risks, the complications and/or the severity of necrotizing enterocolitis in infants and young children and/or relieving the symptoms caused by necrotizing enterocolitis on health in infants and young children suffering from NEC).

The composition according to the invention also allows getting a better gut protection from microbial and pathogen overgrowth, promoting the gut development and maturation, decreasing gut inflammation, promoting the enteral feeding tolerance and/or preventing any diseases and complications associated thereof in infants and young children.

FIGURE

FIG. 1 shows the activation of the inflammation marker and master regulator nuclear factor kappa B (NFkB) upon the stimulation with the pro-inflammatory TNFalpha or a gram negative bacterium (here, *S. typhymurium*) using a NFkB reporter cell line.

DETAILED DESCRIPTION OF THE INVENTION

As used herein, the following terms have the following meanings.

The term "infant" means a child under the age of 12 months.

The expression "young child" means a child aged between one and three years, also called toddler.

An "infant or a young child born by C-section" means an infant or a young child who was delivered by caesarian. It means that the infant or the young child was not vaginally delivered.

A "preterm" or "premature" means an infant or a young child who was not born at term. Generally it refers to an infant or a young child born prior 36 weeks of gestation.

The expression "nutritional composition" means a composition which nourishes a subject. This nutritional composition is usually to be taken orally or intravenously, and it usually includes a lipid or fat source and a protein source.

The expression "hypoallergenic nutritional composition" means a nutritional composition which is unlikely to cause allergic reactions.

In a particular embodiment the composition of the present invention is a "synthetic composition". The expression "synthetic composition" means a mixture obtained by chemical and/or biological means, which can be chemically identical to the mixture naturally occurring in mammalian milks (i.e. the synthetic composition is not breast milk).

The expression "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae).

The expression "starter infant formula" means a foodstuff intended for particular nutritional use by infants during the first four months of life.

The expression "follow-on formula" means a foodstuff intended for particular nutritional use by infants aged over four months and constituting the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The expression "growing-up milk" means a milk-based beverage adapted for the specific nutritional needs of young children.

The expression "fortifier" refers to liquid or solid nutritional compositions suitable for mixing with breast milk or infant formula.

The term "weaning period" means the period during which the mother's milk is substituted by other food in the diet of an infant or a young child.

The expressions "necrotizing enterocolitis" and NEC can be used interchangeably.

The expressions "preventing necrotizing enterocolitis", "preventing NEC" or "prevention of NEC" mean avoiding that NEC occur and/or decreasing the incidence of the NEC (reduction of the frequency, i.e. the number of NEC). It is generally the prevention of NEC occurs during the treatment (i.e. during the administration of the composition of the present invention). It can also encompass the prevention of NEC later in life. The term "later in life" encompasses the effect after the termination of the intervention or treatment. The effect "later in life" can be from 1 week to several months, for example from 2 to 4 weeks, from 2 to 6 weeks, from 2 to 8 weeks, from 1 to 6 months or from 2 to 12 months.

The expressions "treating necrotizing enterocolitis", "treating NEC" or "treatment of NEC" mean decreasing the duration (number of days/weeks/years the infants or young children will suffer from NEC), the risks, the complications and/or the severity of necrotizing enterocolitis such as the consequences and the seriousness of NEC (e.g. high mortality and morbidity rates). This also encompasses the relief of the symptoms caused by necrotizing enterocolitis on health and/or the related effects, especially intestinal necrosis that could lead to resection of a part of the intestine, growth development delay, problems of neurodevelopment, such as a long term neurodevelopment impairment, and/or diminishing the pain and/or easing the sleep and/or stabilizing the activity of infants and young children suffering from NEC.

By the expression "promoting the enteral feeding tolerance" it is meant a decrease or a suppression of phenomena that may occur during the feeding (due to a feeding intolerance) such as regurgitation, diarrhea, nausea.

The term "HMO" or "HMOs" refers to human milk oligosaccharide(s). These carbohydrates are highly resistant to enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "precursor of HMO" is a key compound that intervenes in the manufacture of HMO, such as sialic acid and/or fucose. It is especially a key carbohydrate compound that intervenes in the manufacture of HMO and that is part of the structure of the HMO. In a particular embodiment, the precursor of HMO is chosen from the list consisting of sialic acid, fucose, N-acetyllactosamine (type I or type II) or any mixture thereof. In a specific embodiment, it is sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

A "fucosylated oligosaccharide" is an oligosaccharide having a fucose residue. It has a neutral nature. Some examples are 2-FL (2'-fucosyllactose), 3-FL (3-fucosyllactose), difucosyllactose, lacto-N-fucopentaose I, lacto-N-fucopentaose II, lacto-N-fucopentaose III, lacto-N-fucopentaose V, lacto-N-difucohexaose I, fucosyllacto-N-hexaose, Difucosyllacto-N-hexaose I, Difucosyllacto-N-neohexaose II.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose) and LNnT (lacto-N-neotetraose).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995; 125:1401-12).

The term "probiotic" means microbial cell preparations or components of microbial cells with a beneficial effect on the health or well-being of the host. (Salminen S, Ouwehand A. Benno Y. et al. *"Probiotics: how should they be defined"* Trends Food Sci. Technol. 1999:10 107-10). The microbial cells are generally bacteria or yeasts.

The term "cfu" should be understood as colony-forming unit.

All percentages are by weight unless otherwise stated.

It is noted that the various aspects, features, examples and embodiments described in the present application may be compatible and/or combined together.

In addition, in the context of the invention, the terms "comprising" or "comprises" do not exclude other possible elements.

The present inventors have surprisingly found that a composition comprising a mixture of specific human milk oligosaccharides including LNT is particularly effective for use in promoting enteral feeding tolerance and gut functional maturation and in decreasing the incidence of necrotizing enterocolitis in infants and young children.

Without being bound by theory, the inventors of the present invention believe that the presence of LNT is an important key compound, acting at least in part by way of the commensal gut microbiota, to promote enteral feeding tolerance and gut functional maturation and in the action against NEC. Furthermore LNT may act in synergy with at least a second human milk oligosaccharide and/or precursor thereof.

An object of the invention is a composition comprising lacto-N-tetraose (LNT) and at least another human milk oligosaccharide and/or precursor thereof, for use (or suitable for use) in preventing necrotizing enterocolitis in infants and young children.

Another object of the invention is a composition comprising lacto-N-tetraose (LNT) and at least another human milk oligosaccharide and/or precursor thereof, for use (or suitable for use) in treating necrotizing enterocolitis in infants and young children such as decreasing the duration, the risks, the complications and/or the severity of necrotizing enterocolitis in infants and young children and/or relieving the symptoms caused by necrotizing enterocolitis on health in infants and young children suffering from NEC.

Another object of the invention is a composition comprising lacto-N-tetraose (LNT) and at least another human milk oligosaccharide and/or precursor thereof, for use (or suitable for use) in improving the gut protection from microbial and pathogen overgrowth, in promoting the gut development and maturation, in decreasing gut inflammation, in promoting the enteral feeding tolerance and/or in preventing any diseases and complications associated thereof in infants and young children. The diseases and complications associated thereof are known by the skilled person. It might be for example diarrhea, growth retardation (i.e. delay in the global size of the infants or young children or delay in the size and/or development of any organ or tissue of said infants or young children) . . . .

In some embodiments the composition of the invention can be used for the different above-mentioned uses in combination, for example the composition can be suitable for use in treating necrotizing enterocolitis, in promoting the gut development and maturation, and in promoting the enteral feeding tolerance in infants and young children.

More details will now be given regarding the content and the nature of the composition suitable for these different uses.

The composition according to the invention comprises lacto-N-tetraose (LNT) and at least another human milk oligosaccharide or precursor thereof. It therefore necessarily contains at least two human milk oligosaccharides components, i.e.:
  either at least 2 human milk oligosaccharides (HMOs), one of them being LNT,
  or at least 1 human milk oligosaccharide (LNT) and a precursor thereof (such as sialic acid).

By "at least another human milk oligosaccharide and/or precursor thereof", it is meant that there can be one, two, three, four, five, six or even more other human milk oligosaccharide(s) and/or precursor(s) thereof present in addition to LNT.

In some embodiments the composition according to the invention comprises lacto-N-tetraose (LNT) and only another human milk oligosaccharide or precursor thereof.

In some embodiments the composition according to the invention comprises lacto-N-tetraose (LNT) and two other human milk oligosaccharides and/or precursors thereof.

In some embodiments the composition according to the invention comprises lacto-N-tetraose (LNT) and three other human milk oligosaccharides and/or precursors thereof.

In some embodiments the composition according to the invention comprises lacto-N-tetraose (LNT) and four other human milk oligosaccharides and/or precursors thereof.

In the present invention, said at least another human milk oligosaccharide and/or precursor thereof is selected from the list comprising N-acetylated oligosaccharide (N-acetyl lactosamine or an oligosaccharide containing N-acetyl-lactosamine), sialylated oligosaccharide, fucosylated oligosaccharide, sialic acid, fucose and any combination thereof.

The composition according to the invention necessarily contains at least one N-acetylated oligosaccharide, which is LNT. In some particular examples the composition according to the invention can therefore contain at least a second N-acetylated oligosaccharide such as lacto-N-neotetraose (LNnT).

Thus the composition according to the invention can contain both LNT and LNnT.

LNT and LNnT can be in a similar or a different amount. In some embodiments, the composition according to the invention comprises LNT and LNnT in a ratio LNT:LNnT between 5:1 and 1:2, or from 2:1 to 1:1, or from 2:1.2 to 2:1.6. In some particular embodiments the amount of LNT is higher than the amount of LNnT. Indeed without being bound by any theory it is believed that an amount of LNT which is higher than an amount of LNnT can have some advantageous benefits regarding NEC.

The composition according to the invention can contain from 0.1 to 5 g of N-acetylated oligosaccharide(s)/100 g composition on a dry weight basis or from 0.1 to 3 g of N-acetylated oligosaccharide(s)/100 g composition on a dry weight basis.

In particular examples the composition comprises LNT in an amount of from 0.1 to 4, or from 0.3 to 3 or from 0.4 to 2 or from 0.4 to 1, or from 0.4 to 0.9 g/L of composition. In particular examples the composition comprises LNnT in an amount of from 0.1 to 4, or from 0.2 to 2 or from 0.3 to 1.5 or from 0.4 to 1, or from 0.4 to 0.9 g/L of composition.

LNT and LNnT may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

In some embodiments, the composition according to the invention comprises LNT and at least a sialylated oligosaccharide. There can be one or several sialylated oligosaccharide(s).

For example the sialylated oligosaccharide can be selected from the group comprising 3' sialyllactose (3-SL), 6' sialyllactose (6-SL), and a combination of 3' sialyllactose (3-SL) and 6' sialyllactose (6-SL).

In some particular embodiments the composition comprises LNT, 3-SL and 6-SL. In some particular embodiments the ratio between 3'-sialyllactose (3-SL) and 6'-sialyllactose (6-SL) can be in the range between 5:1 and 1:10, or from 3:1 and 1:1, or from 1:1 to 1:10.

In some other embodiments the composition comprises LNT and 6-SL.

The 3'- and 6'-forms of sialyllactose may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes.

Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

The composition according to the invention can contain from 0.05 to 5 g of sialylated oligosaccharide(s), e.g from 0.1 to 2 g, or from 0.2 to 1 g of sialylated oligosaccharide(s) per 100 g of composition on a dry weight basis.

In particular examples the composition comprises from 0.05 to 5 g/L of sialylated oligosaccharide(s), or from 0.1 to 4 g/L, or from 0.3 to 2 g/L, or from 0.4 to 1.5 g/L, or from 0.4 to 1 g/L of sialylated oligosaccharide(s), for example 0.5 g/L of sialylated oligosaccharide(s) or 0.9 g/L of sialylated oligosaccharide(s).

In some particular embodiments the composition can also comprise from 0.8 to 1.7 g/l of sialylated oligosaccharide(s).

In some embodiments, the composition according to the invention comprises LNT and at least a fucosylated oligosaccharide. There can be one or several fucosylated oligosaccharide(s).

For example the fucosylated oligosaccharide can be selected from the group comprising 2'-fucosyllactose (2-FL), 3-fucosyllactose (3-FL), difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difuco-lacto-N-neohexaose difucosyllacto-N-neohexaose I, difucosyllacto-N-neohexaose II, fucosyl-para-Lacto-N-hexaose, tri-fuco-para-Lacto-N-hexaose land any combination thereof.

In some particular embodiments the fucosylated oligosaccharide comprises a 2' fucosyl-epitope. It can be for example selected from the list comprising 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose, difuco-lacto-N-neohexaose, difucosyllacto-N-neohexaose, fucosyl-para-Lacto-N-hexaose and any combination thereof.

In some particular embodiments the composition comprises LNT and 2'-fucosyllactose (2-FL).

The fucosylated oligosaccharide may be isolated by chromatography or filtration technology from a natural source such as animal milks. Alternatively, it may be produced by biotechnological means using specific fucosyltransferases and/or fucosydase either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

The composition according to the invention can contain from 0.1 to 10 g of fucosylated oligosaccharide(s) per 100 g of composition on a dry weight basis, e.g. from 0.1 to 8 g, or from 0.1 to 4 g, or from 0.5 to 3 g of fucosylated oligosaccharide(s) per 100 g of composition on a dry weight basis.

In particular examples the composition comprises from 0.5 to 10 g/L of fucosylated oligosaccharide(s), or from 0.5 to 5 g/L, or from 1 to 4.5 g/L, or from 2 to 4 g/L, or from 2.5 to 3.5 g/L of fucosylated oligosaccharide(s). The amount of fucosylated oligosaccharide(s) will be adapted depending on the needs of the infant or young child. In some examples, the composition can comprise from 0.5 to 2 g/L or from 0.7 to 1.8 g/L of fucosylated oligosaccharide(s). In some other examples, the composition can comprise higher levels of fucosylated oligosaccharide(s) such as from 5 to 10 g/L or from 6 to 8 g/L of fucosylated oligosaccharide(s).

In a particular embodiment, the composition of the invention comprises from 0.15 to 9 g of the total amount of N-acetylated oligosaccharide(s), sialylated oligosaccharide(s) and fucosylated oligosaccharide(s) per 100 g of composition, e.g. from 0.2 to 8 g per 100 g of composition, e.g. from 0.5 to 7 g per 100 g of composition, e.g. from 1 to 5 g per 100 g of composition.

In some particular embodiments the composition according to the invention comprises LNT with at least a precursor of human milk oligosaccharide. The precursor is a key compound that intervenes in the manufacture of HMO, such as sialic acid and/or fucose. There can be one or several precursor(s) of human milk oligosaccharide.

In some specific embodiments the composition of the invention comprises LNT and sialic acid.

The composition according to the invention can comprise from 0 to 2.3 g of precursor(s) of human milk oligosaccharide per 100 g of composition on a dry weight basis e.g from 0 to 1.5 g or from 0 to 0.8 g of precursor(s) of human milk oligosaccharide per 100 g of composition on a dry weight basis.

In particular examples the composition comprises from 0 to 3 g/L of precursor(s) of human milk oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of human milk oligosaccharide.

In some particular embodiments the composition according to the invention comprises LNT and at least another human milk oligosaccharide and/or precursor thereof which is selected from the list comprising lacto-N-neotetraose (LNnT), 3' sialyllactose (3-SL), 6' sialyllactose (6-SL), 2'-fucosyllactose (2-FL), sialic acid and any combination thereof.

In some particular embodiments the composition according to the invention comprises LNT, lacto-N-neotetraose (LNnT), 6' sialyllactose (6-SL), 2'-fucosyllactose (2-FL) and optionally sialic acid.

In some specific embodiments, the lacto-N-tetraose (LNT) and each of said at least another human milk oligosaccharide and/or precursor thereof are each ones present in an amount from 0.1 to 20 g/L of said composition, e.g. from 0.1 to 5 g/L of said composition.

In a particular example the composition according to the invention comprises:
from 0.5 to 10 g/L of 2FL
from 0.1 to 4 g/L of LNnT
from 0.1 to 4 g/L of LNT
from 0.1 to 4 g/L of 6SL
from 0 to 3 g/L of sialic acid In a particular example the composition according to the invention comprises:
from 2 to 4 g/L of 2FL
from 0.3 to 1.5 g/L of LNnT
from 0.4 to 2 g/L of LNT
from 0.3 to 1 g/L of 6SL
from 0 to 0.5 g/L of sialic acid In a particular example the composition according to the invention comprises:
3 g/L of 2FL
0.5 g/L of LNnT
0.65 g/L of LNT
0.5 g/L of 6SL
0.13 g/L of sialic acid In a particular example the composition according to the invention comprises:
3 g/L of 2FL
0.5 g/L of LNnT
0.65 g/L of LNT
0.5 g/L of 6SL
0 g/L of sialic acid The composition of the invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM I-2116, *Lactobacillus johnsonii* CNCM I-1225, *Streptococcus salivarius* DSM 13084 sold by BLIS Technologies Limited of New Zealand under the designation KI2, *Bifidobacterium lactis* CNCM I-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The composition according to the invention typically contains from 10e3 to 10e12 cfu of probiotic strain, more preferably between 10e7 and 10e12 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The composition of the invention can further comprise at least one non-digestible oligosaccharide (e.g. prebiotics) other than the human milk oligosaccharides previously mentioned. They are usually in an amount between 0.3 and 10% by weight of composition.

Prebiotics are usually non-digestible in the sense that they are not broken down and absorbed in the stomach or small intestine and thus remain intact when they pass into the colon where they are selectively fermented by the beneficial bacteria. Examples of prebiotics include certain oligosaccharides, such a fructooligosaccharides (FOS) and galactooligosaccharides (GOS). A combination of prebiotics may be used such as 90% GOS with 10% short chain fructooligosaccharides such as in the product by BENEO-Orafti sold under the trademark ORAFTI® oligofructose (previously RAFTILOSE®) or 10% inulin such as in the product sold by BENEO-Orafti under the trademark ORAFTI® inulin (previously RAFTILOSE®). A particularly preferred combination of prebiotics is 70% short chain fructo-oligosaccharides and 30% inulin, which is a product sold by BENEO-Orafti under the trademark PREBIO 1.

The composition of the invention can further comprise at least one phage (bacteriophage) or a mixture of phages, preferably directed against pathogenic Streptococci, *Haemophilus, Moraxella* and Staphylococci.

The composition is typically used in infants and young children.

In some embodiments the composition according to the invention can be for use before and/or during the weaning period.

The composition according to the invention can be a nutritional composition, a preparation or a food product.

The composition according to the invention can be for example a nutritional composition such as a synthetic nutritional composition. It can be an infant formula, a starter infant formula, a follow-on formula, a baby food, an infant cereal composition, a growing-up milk, a fortifier such as a human milk fortifier, or a supplement. When the composition is a supplement, it can be provided in the form of unit doses.

In some embodiments the composition of the present invention is typically an infant formula.

The composition according to the invention can be used in term or preterm infants or young children.

Advantageously the composition of the invention is for use in preterm infants or young children.

Advantageously the composition according to the invention can also be used in infants or young children born by C-section.

In some embodiments the composition of the invention is for use in infants who are preterm, small for gestational age and/or born by C-section.

In some embodiments the composition of the invention is advantageously for use in infants or young children who are preterm and born by C-section.

The human milk oligosaccharides components (i.e. the human milk oligosaccharide(s) and optionally the precursor (s) thereof) may be administered in the same composition or may be administered sequentially.

The composition of the present invention can be in solid (e.g. powder), liquid or gelatinous form. If the age group of 0 to 12 months of life is to be addressed, the composition is preferably a nutritional composition consumed in liquid form. It may be a nutritionally complete formula such as an infant formula, a starter formula, a follow-on formula, a growing-up milk or a fortifier such as a human milk fortifier. Alternatively for the young children group, the composition may be for example a juice drink, any other chilled or shelf stable beverage, a soup, a baby food, or an infant cereal composition.

The composition according to the invention generally also contains a protein source, preferably in an amount below 2.0 g per 100 kcal, even more preferably in an amount below 1.8 g per 100 kcal. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component peptides or amino acids.

The proteins may be either fully or partially hydrolysed. It may be desirable to supply partially hydrolysed proteins (degree of hydrolysis between 2 and 20%), for example for infants believed to be at risk of developing cow's milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In a particular embodiment the composition according to the invention is a hypoallergenic composition. In another particular embodiment the composition according to the invention is a hypoallergenic nutritional composition.

The composition according to the present invention generally contains a carbohydrate source. This is particularly preferable in the case where the nutritional composition of the invention is an infant formula. In this case, any carbohydrate source conventionally found in infant formulae such as lactose, saccharose, maltodextrin, starch and mixtures thereof may be used although the preferred source of carbohydrates is lactose.

The composition according to the present invention generally contains a source of lipids. This is particularly relevant if the nutritional composition of the invention is an infant formula. In this case, the lipid source may be any lipid or fat which is suitable for use in infant formulae. Preferred fat sources include palm oleic, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source preferably has a ratio of n–6 to n–3 fatty acids of about 5:1 to about 15:1; for example about 8:1 to about 10:1.

The composition of the invention also contains preferably all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the composition of the invention may contain emulsifiers and stabilisers such as soy, lecithin, citric acid esters of mono- and di-glycerides, and the like.

The composition of the invention may also contain other substances which may have a beneficial effect such as lactoferrin, nucleotides, nucleosides, and the like.

The composition according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The LNT and the other human milk oligosaccharide(s) and/or precursor(s) thereof will be added at this stage if the final product is to have a liquid form.

If the final product is to be a powder, the oligosaccharide components may likewise be added at this stage if desired. The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The LNT and the other human milk oligosaccharide(s) and/or precursor(s) thereof may be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement including the LNT and the other human milk oligosaccharide(s) and/or precursor(s) in an amount sufficient to achieve the desired effect in an individual. This form of administration is more suited to older children and adults. The daily dose of N-acetylated oligosaccharide(s) is typically from 0.1 to 3 g, the daily dose of the sialylated oligosaccharide(s) is typically from 0.1 to 2 g, and the daily dose of the fucosylated oligosaccharide(s) is typically from 0.1 to 4 g.

The amount of oligosaccharides to be included in the supplement will be selected according to the manner in which the supplement is to be administered. For example, if the supplement is to be administered twice a day, each supplement may contain from 0.05 to 1.5 g of N-acetylated oligosaccharide(s), from 0.05 to 1 g of sialylated oligosaccharide(s), and from 0.05 to 2 g of fucosylated oligosaccharide(s).

The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The composition can be administered (or given) at an age and for a period that depends on the needs. In some embodiments the composition of the invention is given immediately after birth. In some embodiments the composition of the invention is given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first 2 years of life or even more.

In some embodiments, the composition of the invention is given few days, or few weeks, or few months after birth. This may be especially the case when the infant is premature, but not necessarily.

The composition of the invention can be given for some days (1, 2, 3, 4, 5, 6 . . . ), or for some weeks (1, 2, 3, 4, 5, 6, 7, 8 or even more), or for some months (1, 2, 3, 4, 5, 6, 7, 8, 9, 10, 11 or even more), or for some years (1, 2 . . . ) depending on the needs.

The composition according to the invention can also allow reducing the hospital stay and the overall health/medical costs.

The present invention also relates to the use of lacto-N-tetraose (LNT) and at least another human milk oligosaccharide and/or precursor thereof, in the preparation of a composition to be administered in infants and young children for preventing necrotizing enterocolitis in infants and young children and/or for treating necrotizing enterocolitis in infants and young children (such as decreasing the duration, the risks, the complications and/or the severity of necrotizing enterocolitis in infants and young children and/or relieving the symptoms caused by necrotizing enterocolitis on health in infants and young children suffering from NEC).

The present invention also relates to the use of lacto-N-tetraose (LNT) and at least another human milk oligosaccharide and/or precursor thereof, in the preparation of a composition to be administered in infants and young children for improving the gut protection from microbial and pathogen overgrowth, for promoting the gut development and maturation, for decreasing gut inflammation, for promoting the enteral feeding tolerance and/or for preventing any diseases and complications associated thereof in infants and young children.

The present invention also relates to a method for preventing necrotizing enterocolitis in infants and young children and/or for treating necrotizing enterocolitis in infants and young children (such as decreasing the duration, the risks, the complications and/or the severity of necrotizing enterocolitis in infants and young children and/or relieving the symptoms caused by necrotizing enterocolitis on health in infants and young children suffering from NEC), said method comprising administering to said infants and young children a composition comprising lacto-N-tetraose (LNT) and at least another human milk oligosaccharide and/or precursor thereof.

The present invention also relates to a method for improving the gut protection from microbial and pathogen overgrowth, for promoting the gut development and maturation, for decreasing gut inflammation, for promoting the enteral feeding tolerance and/or for preventing any diseases and complications associated thereof in infants and young children, said method comprising administering to said infants and young children a composition comprising lacto-N-tetraose (LNT) and at least another human milk oligosaccharide and/or precursor thereof.

The different embodiments, details and examples previously described in the specification can similarly be applied to these uses and methods.

EXAMPLES

The following examples illustrate some specific embodiments of the composition for use according to the present invention. The examples are given solely for the purpose of illustration and are not to be construed as limitations of the present invention, as many variations thereof are possible without departing from the spirit of the invention.

Example 1

An example of the composition of an infant formula according to the present invention is given in the below table 1. This composition is given by way of illustration only.

TABLE 1 an example of the composition of an infant formula according to the present invention

| Nutrient | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| 2FL (g) | 0.44 | 3 |
| LNT (g) | 0.1 | 0.65 |
| LNnT (g) | 0.08 | 0.5 |
| 6'sialyllactose (g) | 0.08 | 0.5 |

Example 2

HT29 cells harbouring an expression plasmid with the NFkB promoter controlling an alkaline phosphatase were treated with different media and challenged with the proinflammatory TNFalpha or a gram negative bacterium such as *Salmonella typhimurium*. Treatments were cell culture media fermented with *Bifidobacterium longum* subsp *infantis* and (i) lactose or (ii) Lacto-N-tetraose (LNT).

The cells harbored an expression plasmid with the NF-κB promoter controlling an alkaline phosphatase so that stimulation by TNF-α or a gram negative bacterium would be indicated by fluorescence generated by interaction of the alkaline phosphatase with a fluorogenic substrate. Results are shown in FIG. 1. FIG. 1 shows the activation of the inflammation marker and master regulator nuclear factor kappa B (NFkB) upon the stimulation with the pro-inflammatory TNFalpha or a gram negative bacterium (here, *S. typhymurium*) using a NFkB reporter cell line. In presence of cell culture media fermented with the infant gut commensal bacterium *Bifidobacterium longum* subsp *infantis* and lactose (control) a very strong stimulation was seen, while in presence of cell culture media fermented with *Bifidobacterium longum* subsp *infantis* and Lacto-N-tetraose (LNT) no stimulation was observed. This indicates LNT to exert a strong anti-inflammatory effect. Conditioned media with LNT lead to higher resistance of the cells upon proinflammatory TNFalpha or a gram negative bacterial stimulation. Intestinal epithelia cells in media conditioned by LNT (lacto-N-tetraose) and *Bifidobacterium* fermentation products are more resistant to proinflammatory stimulation by TNFalpha as compared to cells in a control medium conditioned by lactose and *Bifidobacterium* fermentation products.

This suggests the importance of the role of LNT in the modulation of the immune homeostasis and in the maturation of immune responses and the reduction of inflammatory diseases such as occurring strongly in NEC, in a neonatal infant.

Example 3

Objectives and Study

Human milk oligosaccharides (HMO) may mediate a major part of the known prebiotic and anti-inflammatory effect of human milk in the newborn intestine.

With the aim to show maturational and immunological effects, it will be important to demonstrate effects in a suitable in vivo model showing marked characteristics of gut immaturity and dysregulated immunity. Preterm piglets have recently been well documented to be excellent models to show extreme sensitivity to the beneficial factors in mother's milk. This model allows for detailed manipulations of feeding practices (enteral, parenteral feeding) and show clear clinical manifestations (necrotizing enterocolitis) in response to suboptimal diets.
Method:

For five days after birth, caesarian-delivered preterm pigs were fed increasing doses (3-15 mL/kg/3 h) of a maltodextrin-based enteral milk formula, with (n=17) or without (n=15) the following HMOs mixture (4.78 g/L formula).

TABLE 2 composition of the tested HMOs mixture

| HMO or precursor thereof | Concentration of the HMO or precursor thereof expressed in g/l of the composition | | Amount of the HMO or precursor thereof expressed in wt % of the oligosaccharide mixture | Ratio LNT:LNnT | Type of HMO |
|---|---|---|---|---|---|
| 2FL | 3 | | 62.8 | | neutral |
| LNnT | 0.5 | 1.15 | 10.5 | 1.3 | neutral N- |
| LNT | 0.65 | | 13.6 | | acetylated |
| 6SL | 0.5 | | 10.5 | | charged sialylated |
| Sialic acid | 0.13 | | 2.6 | | |
| Total | 4.78 | | 100 | | |

Clinical conditions, NEC lesions, amount of mucosa and organ weights were recorded on day 5.
Results:

Mean NEC incidence was lower in the HMO group relative to controls (35% vs 53%). Mucosal weight in the proximal intestine was elevated in the HMO pigs (p<0.05) while body weight, organ weights and diarrhea scores were similar.

CONCLUSION

A diet of a HMO-enriched formula according to the invention, given just after birth on caesarian-delivered preterm pigs seems to induce a positive effect on NEC incidence. This formula seems to improve the short-term resistance to necrotizing enterocolitis (NEC) in these pigs, without involving any apparent adverse effects. This could especially be due to the presence of LNT and its potential synergy with the other human-milk oligosaccharide(s) and/or precursor(s) thereof.

Similar conclusions could be drawn for another experiment made without the addition of sialic acid.

The invention claimed is:

1. A method for treating necrotizing enterocolitis and/or decreasing incidence of necrotizing enterocolitis in an infant or young child in need thereof, the method comprising administering to the infant or young child a composition comprising 2'-fucosyllactose (2-FL), 6' sialyllactose (6-SL), and N-acetylated oligosaccharides comprising lacto-N-tetraose (LNT) and lacto-N-neotetraose (LNnT) in a ratio of LNT:LNnT between 2:1 and 1:1, wherein the LNT is present in an amount from 0.4 to 2 g/L of the composition, and the 2'-fucosyllactose (2-FL), the 6'sialyllactose (6-SL), the lacto-N-tetraose (LNT) and the lacto-N-neotetraose (LNnT) are the only human milk oligosaccharides in the composition.

2. The method according to claim 1, wherein the infant or young child is an infant, and the composition is administered to the infant during the first week after birth of the infant.

3. The method according to claim 1, wherein the composition is administered in an amount that provides a daily dose of 0.1 to 2 g of the 6-SL and 0.1 to 4 g of the 2-FL.

4. The method according to claim 1, wherein the composition is administered in an amount that provides a daily dose of the N-acetylated oligosaccharides of 0.1 to 3 g.

5. The method according to claim 1, wherein the composition further comprises sialic acid.

6. The method according to claim 1, wherein the lacto-N-neotetraose (LNnT) is present in an amount from 0.2 to 2 g/L of the composition.

7. The method according to claim 1, wherein the composition further comprises at least one probiotic in an amount of from $10^3$ to $10^{12}$ cfu/g of the composition (dry weight).

8. The method according to claim 1, wherein the composition is in a form selected from the group consisting of an infant formula, a starter infant formula, a follow-on infant formula, a baby food, an infant cereal composition, a growing-up milk, a fortifier and a supplement.

9. The method according to claim 1, wherein the composition is administered to the infant or young child before and/or during the weaning period.

10. The method according to claim 1, wherein the infant or young child is selected from the group consisting of preterm infants, small for gestational age infants, and infants born by C-section.

11. The method according to claim 1, wherein the infant or young child has necrotizing enterocolitis, and the composition is administered to the infant or young child in an amount effective to treat necrotizing enterocolitis.

12. The method according to claim 1, wherein the LNT is present in an amount from 0.4 to 1 g/L of the composition.

13. The method according to claim 1, wherein the LNT is present in an amount from 0.4 to 0.9 g/L of the composition.

* * * * *